(12) United States Patent
Maynard et al.

(10) Patent No.: US 8,221,317 B2
(45) Date of Patent: Jul. 17, 2012

(54) EXPANDING CANNULA AND RETRACTOR DEVICE AND METHODS OF USE

(75) Inventors: Michael Maynard, New York, NY (US); Joseph Lipman, New York, NY (US)

(73) Assignee: Hospital for Special Surgery, New York, NY (US)

( * ) Notice: Subject to any disclaimer, the term of this patent is extended or adjusted under 35 U.S.C. 154(b) by 130 days.

(21) Appl. No.: 12/712,189

(22) Filed: Feb. 24, 2010

(65) Prior Publication Data

US 2010/0274095 A1    Oct. 28, 2010

Related U.S. Application Data

(60) Provisional application No. 61/155,009, filed on Feb. 24, 2009.

(51) Int. Cl.
*A61B 1/32* (2006.01)

(52) U.S. Cl. ......... 600/208; 600/204; 600/210; 606/198

(58) Field of Classification Search .................. 606/170, 606/167, 192, 198, 194, 207; 604/104–109; 600/208, 206, 215, 205, 204, 207, 210
See application file for complete search history.

(56) References Cited

U.S. PATENT DOCUMENTS

| | | | | |
|---|---|---|---|---|
| 3,044,461 A | * | 7/1962 | Murdock | 600/208 |
| 4,043,338 A | * | 8/1977 | Homm et al. | 604/105 |
| 5,002,557 A | | 3/1991 | Hasson | |
| 5,197,971 A | | 3/1993 | Bonutti | |
| 5,318,012 A | * | 6/1994 | Wilk | 600/205 |
| 5,637,097 A | | 6/1997 | Yoon | |
| 5,836,913 A | * | 11/1998 | Orth et al. | 604/107 |
| 5,888,196 A | * | 3/1999 | Bonutti | 600/204 |
| 6,524,283 B1 | | 2/2003 | Hopper et al. | |
| 6,632,197 B2 | * | 10/2003 | Lyon | 604/107 |

* cited by examiner

*Primary Examiner* — Pedro Philogene
(74) *Attorney, Agent, or Firm* — Leason Ellis LLP

(57) ABSTRACT

Expanding cannula and retractor devices and methods of use are provided. An expanding cannula and retractor device includes a first tube, a second tube positioned within the first tube, and an expandable continuous membrane connecting distal portions of the first and second tubes. The membrane can expand into an annulus based on the movement of the second tube relative to the first tube in order to contact tissue and maintain the position of the device.

24 Claims, 12 Drawing Sheets

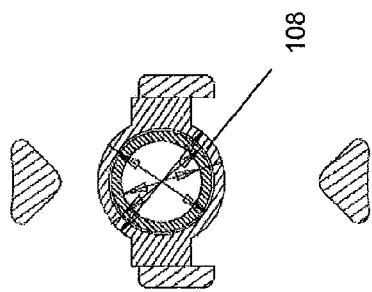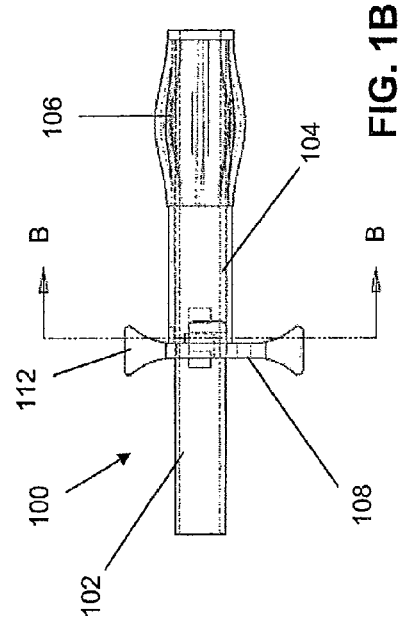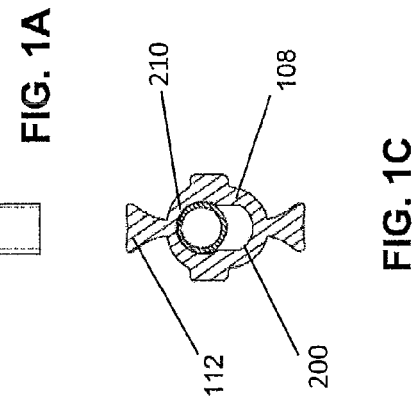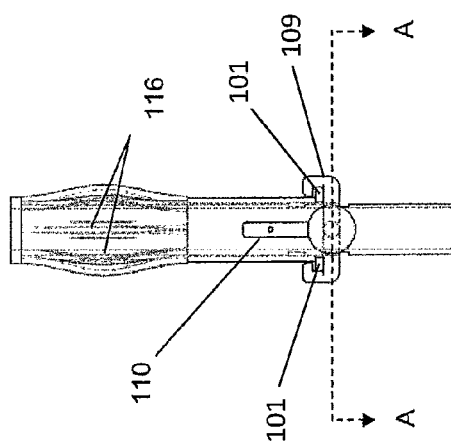

SECTION C

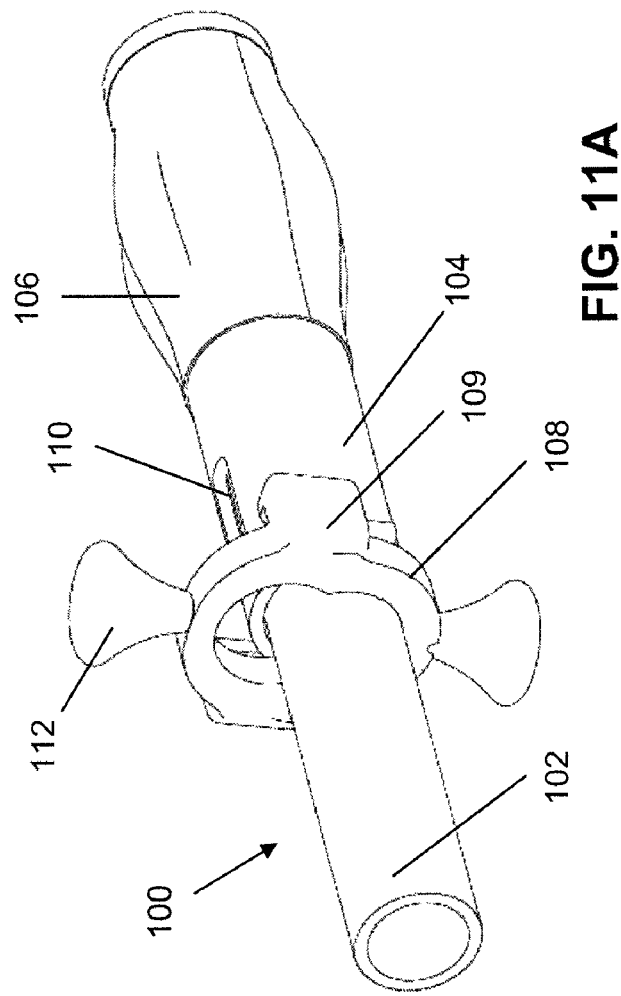
FIG. 11A
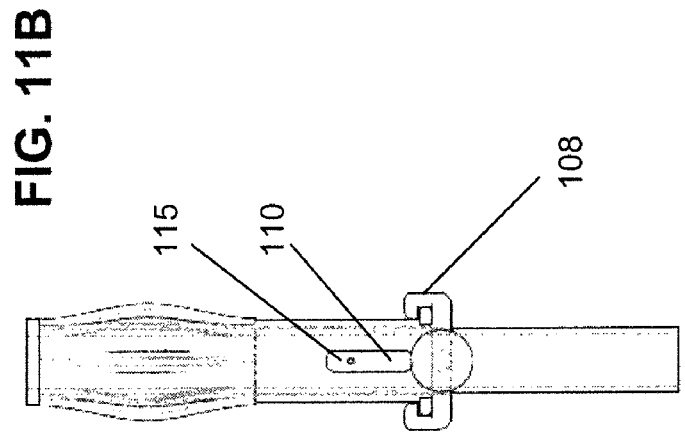
FIG. 11B
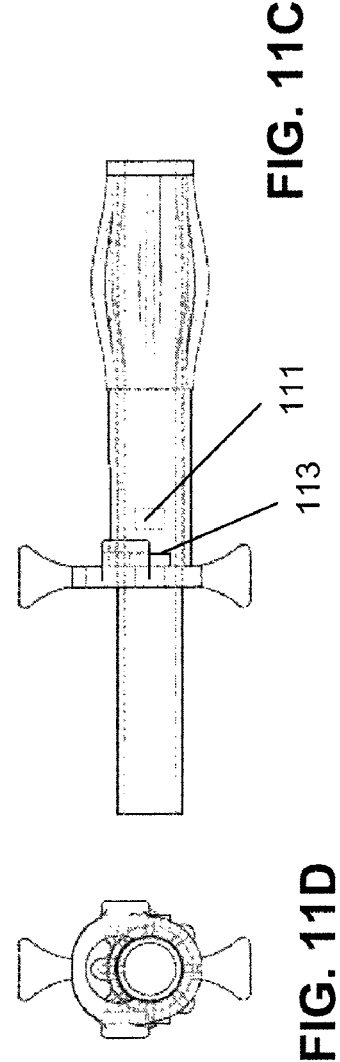
FIG. 11C
FIG. 11D

EXPANDING CANNULA AND RETRACTOR DEVICE AND METHODS OF USE

CROSS-REFERENCE TO RELATED APPLICATION

This application claims priority under 35 U.S.C. §119(e) to U.S. Provisional Application Ser. No. 61/155,009, filed on Feb. 24, 2009, which is hereby incorporated by reference herein in its entirety.

BACKGROUND

Existing cannula devices for providing a portal for arthroscopic and/or laparoscopic surgery are capable of expansion in order to maintain the portal within the tissue into which it has been inserted.

One approach is to include one or more inflatable balloons that are adhesively attached to another instrument. Another approach is a laparoscopic cannula having a distal end that is similar to a "molly bolt," and is made up of slats. Tissue may be trapped within the openings of the slats during retraction of the device since the distal end portion is discontinuous. The expandable portion of the device is attached to, or is part of, a single outer cannula. Yet another approach is a laparoscopic cannula having an outer disposable part and an inner reusable part that is made of metal. A balloon is provided that is inflated and deflated via a syringe and a stop-cock. Still another approach is an arthroscopic retractor that uses the relative movement of concentric tubes to deploy and retract an expandable distal portion. The expandable portion of the retractor is made of slats or arms, and may be accompanied by an inflatable bladder/balloon. The inflatable bladder/balloon is made of a softer material and requires inflation and deflation through a separate port.

Accordingly, it would be desirable to provide a cannula that does not require external inflation or deflation, and that does not trap tissue upon retraction of the cannula.

SUMMARY

An expanding cannula and retractor device and methods of use are provided.

In some embodiments, an expanding cannula and retractor device for insertion through tissue is provided. The device includes a first tube, a second tube disposed within the first tube, and a continuous membrane disposed between and connecting a distal portion of the first tube to a distal portion of the second tube. The membrane expands into an annulus by the relative movement of the second tube with respect to the first tube. The annulus is configured to contact the tissue to maintain the position of the device with respect to the tissue.

In one example, the first tube remains stationary and movement of the second tube causes the membrane to expand into an annulus. In another example, the second tube remains stationary and movement of the first tube causes the membrane to expand into an annulus.

In another example, following the formation of the annulus, the membrane contracts by the relative movement of the second tube with respect to the first tube. For example, the first tube can remain stationary and movement of the second tube can cause the membrane to contract. In still another example, the second tube can remain stationary and movement of the first tube can cause the membrane to contract.

In yet another example, the second tube is disposed concentrically within the first tube. In still another example, the continuous membrane comprises a tubular insert disposed between the first and second tubes, the insert having a plurality of ridges extending along the length of the insert. In yet another example, the tubular insert spans about 20% of the length of the device. In still another example, the annulus is formed by the compression of the tubular insert. In yet another example, the ridges prevent the membrane from folding over itself during formation of the annulus.

In another example, the device includes a clip that is slidably mounted on the first tube. The clip may be, for example, coupled to the second tube. In one example, the clip may be coupled to the second tube through an opening in the second tube. Movement of the clip controls the relative movement of the second tube with respect to the first tube. In still another example, first tube includes a recess that spans a distance on an outer surface of the first tube, the distance corresponding to the distance travelled by the second tube to fully expand the membrane into an annulus. In yet another example, movement of the clip along the first tube in the direction of the distal portion of the first tube causes the membrane to expand into an annulus from a resting position. In still another example, movement of the clip away from the distal portion of the first tube causes the membrane to contract into a resting position.

In still another example, the device includes a locking mechanism coupled to the clip. In one example, the locking mechanism prevents the clip from sliding along the first tube when engaged. In another example, the locking mechanism prevents the membrane from expanding or contracting when engaged.

In yet another example, the first and second tubes are constructed from a rigid plastic material or a metallic material. In still another example, the outside diameters of the first and second tubes range from 5-10 mm. In yet another example, the membrane is constructed from a flexible rubber material or a silicon material.

In accordance with the disclosed subject matter, an expanding cannula and retractor device and methods of use are provided.

BRIEF DESCRIPTION OF THE DRAWINGS

In the drawings,

FIGS. 1A and 1B are perspective views of an illustrative expanding cannula and retractor device in accordance with some embodiments of the disclosed subject matter;

FIGS. 1C and 1D are sectional views of the expanding cannula and retractor device of FIGS. 1A and 1B in accordance with some embodiments of the disclosed subject matter;

FIGS. 11A-11D are perspective, side, and sectional views illustrating a locked position for a clip of an expanding cannula and retractor device in accordance with some embodiments of the disclosed subject matter.

DETAILED DESCRIPTION

Figure 2A:
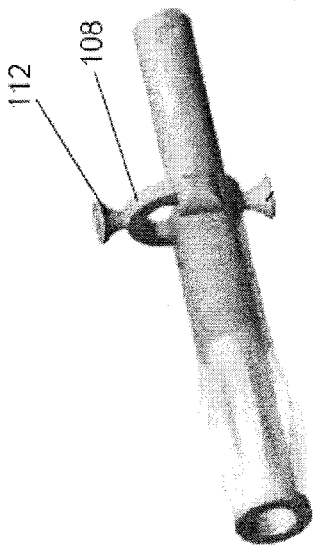
FIGS. 2A-2C are perspective views of an illustrative expanding cannula and retractor device in accordance with some embodiments of the disclosed subject matter.

An expanding cannula and retractor device and methods of use are provided. In accordance with the disclosed subject matter, the device can be used as a portal of entry and a retractor. The device disclosed herein has a continuous, expandable surface that is mechanically deployed and relaxed without the need for external inflation or deflation.

The continuous, expandable portion of the device precludes the trapping of tissue upon retraction of the device. The mechanical deployment and retraction of the expandable surface provides for reliable deployment and retraction with a reduced chance for failure of the system. The device disclosed herein may be used, for example, in arthroscopic or laparoscopic surgery.

The following FIGS. 1A-12D and their accompanying descriptions provide detailed examples of the implementation of the devices and methods disclosed herein.

FIGS. 1A and 1B are perspective views of an illustrative expanding cannula and retractor device in accordance with some embodiments of the disclosed subject matter. FIGS. 1C and 1D are sectional views of the expanding cannula and retractor device of FIGS. 1A and 1B in accordance with some embodiments of the disclosed subject matter. As shown in FIGS. 1A-1B, cannula and retractor device 100 includes a first tube 102, a second tube 104, and a continuous, flexible membrane 106 disposed between first tube 102 and second tube 104. Cannula and retractor device 100 may be referred to interchangeably herein as cannula 100, retractor 100, cannula and retractor device 100, or device 100. Second tube 104 provides the outer body of device 100 for penetrating skin and tissue for arthroscopic and laparoscopic procedures. First tube 102 is concentrically positioned within second tube 104 and provides the inner body of device 100 for receiving and guiding instruments for arthroscopic and laparoscopic procedures (e.g., a catheter).

In some embodiments, first and second tubes 102 and 104 may be fabricated from, for example, a rigid plastic (e.g., PVC) or a metallic material. These materials are merely illustrative, and first and second tubes 102 and 104 may be constructed from any suitable material.

In some embodiments, first and second tubes 102 and 104 may each have outer diameters ranging from between 5 mm and 10 mm. These diameters are merely illustrative, and first and second tubes 102 and 104 may have any suitable outer or inner diameters. For example, the outer and inner diameters may vary depending on the application in which the device 100 is used.

Membrane 106 is positioned between first tube 102 and second tube 104, and connects the distal portion of first tube 102 to the distal portion of second tube 104. Membrane 106 has an expanded position in which it forms an annulus 114, as shown, for example, in FIGS. 6, 7 and 10. Membrane 106 achieves the expanded position when first and second tubes 102 and 104 move relative to each other. As shown, for example, in FIGS. 1A and 1B, membrane 106 also has a resting position in which the membrane is unexpanded and includes a plurality of ridges 116.

Expansion and contraction of membrane 106 is mechanically fixed by clip 108. As shown by FIGS. 1A-1D, clip 108 is slidably mounted onto the outer surface of the second tube 104, and may be coupled to the first tube 102. Clip 108 may be coupled to first tube 102 through, for example, an opening in, the first tube 102. This configuration allows first tube 102 to move within second tube 104 while second tube 104 remains stationary by sliding clip 108 along the outer surface of second tube 104. The movement of second tube 104 relative to first tube 102 causes the expansion and contraction of membrane 106. Alternatively, the expansion and contraction of membrane 106 could be caused by movement of second tube 104 while first tube 102 remains stationary. In order to accommodate movement of clip 108 and first tube 102, second tube 104 may include a recess 110 that spans a distance on the outer surface of second tube 104 corresponding to the distance that first tube 102 must travel to fully expand membrane 106 into annulus 114. Clip 108 may include a extending portions 112 which allow a user to slide clip 108 along device 100.

Figure 2B:
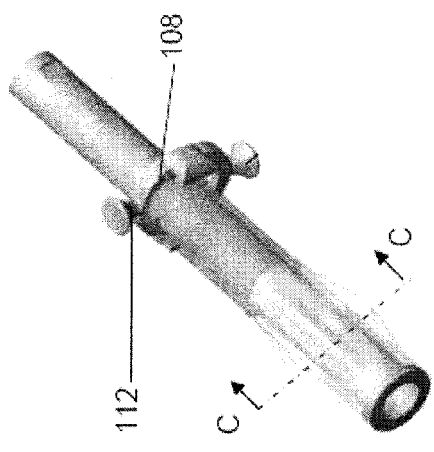
Figure 2C:
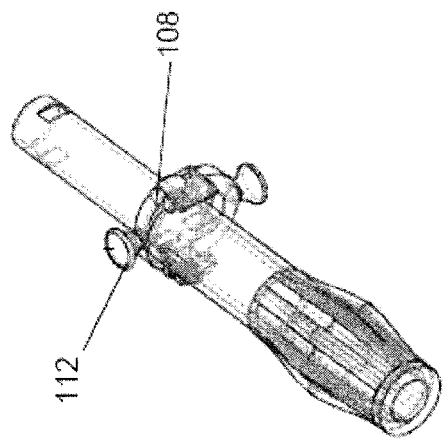
Figure 2D:
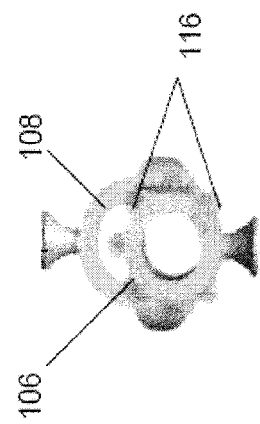
FIG. 2D is a sectional view of the illustrative expanding cannula and retractor device of FIGS. 2A-2C in accordance with some embodiments of the disclosed subject matter.

FIGS. 2A-2C are perspective views of an illustrative expanding cannula and retractor device in accordance with some embodiments of the disclosed subject matter. FIG. 2D is a sectional view of the expanding cannula and retractor device of FIG. 2B in accordance with some embodiments of the disclosed subject matter. FIGS. 2A-2D further illustrate the configuration of first and second tubes 102 and 104 and clip 108. Clip 108 may be, for example, approximately 35 mm in height, and extending portions 112 may each have a width of approximately 9.65 mm. Clip 108 may have, for example, an outer diameter of approximately 12.7 mm and an inner diameter of approximately 10.5 mm. These dimensions of clip 108 are merely illustrative, and the clip may have any suitable combination of dimensions.

FIGS. 11A-11D are perspective, side, and sectional views illustrating a locked position for a clip of an expanding cannula and retractor device in accordance with some embodiments of the disclosed subject matter. FIGS. 12A-12D are perspective, side, and sectional views illustrating an unlocked position for a clip of an expanding cannula and retractor device in accordance with some embodiments of the disclosed subject matter. As shown in FIGS. 11A-11D, clip 108 may include locking portions 109 for engagement with slots 111 and 113. As shown in the figures, slots 111, 113 are formed in the outer surface of the inner first tube 102 in spaced relationship. As shown in the figures (e.g., FIG. 1C), a center opening of the clip has an irregular shape in that a first (lower) section 200 has a reduced width compared to a second (upper) section 210 which has a great width. As shown in FIG. 1D, the second section 210 has a circular shape for receiving a circular shaped section of the inner tube 102, while the first section 200 does not have a circular shape and is of reduced width, thereby preventing reception of the circular shaped section of the inner tube 102. However, when the inner tube 102 is properly aligned with the clip 108 such that one of the slots 111, 113 is in registration with the clip 108, the clip 108 can be moved from the second section 210 of the clip 200 to the first section 200 of the clip 108 since the portion of the inner tube 102 with slots 111, 113 is of reduced diameter and has a complementary shape. When the inner tube 102 is disposed in the lower first section 200 of the clip 108, it is locked in place and cannot be moved axially relative to the outer tube 104. When locking portions 109 are engaged with slots 111 (not shown), for example, device 100 is locked in the expanded position. When locking portions 109 are engaged with slots 113, for example, device 100 is locked in the resting position. To engage slots 111 and 113, clip 108 moves up and down on an axis perpendicular to the axes of first and second tubes 102 and 104. As shown in the figures, the outer tube 104 includes tabs 101 extending radially outward from the outer tube 104. As shown, each locking portion 109 has an inwardly directed finger portion spaced from the clip body. The tab 101 is received (captured) within this space between the finger portion of the clip 108 and the clip body. As shown in the figures, the up and down movement of the clip 108 causes the clip portion 108 (i.e., finger portions thereof) to ride along the tab 101. The relationship between the tabs 101 and locking portions 109 thus locate the position of the clip on the outer tube 104 and restricts the type of permitted movement between the two parts. As shown in FIGS. 12A-12D, device 100 is unlocked when section 210 of the clip 108 is disengaged from slots 111 or 113. In this position, device 100 may be deployed into annulus 114 or contracted into a resting position. As shown in FIGS. 11A-11D and 12A-12D, the inner tube 102 of the device 100 may include a pin 115 disposed within recess 110 that prevents the tubes from translating too far relative to one another. For example, pin 115 may abut the end of recess 110 to prevent further relative movement of the first and second tubes 102 and 104. This abutment prevents over-expansion of annulus 114.

Section 210 of the clip 108 is merely one example of a mechanism to prevent inadvertent movement of clip 108 and any resultant, unwanted expansion or contraction of membrane 106 during a procedure. The embodiments disclosed herein may be used with any other suitable mechanism for locking first and second tubes 102 and 104 relative to each other to prevent the deployment of annulus 114.

Figure 3B:
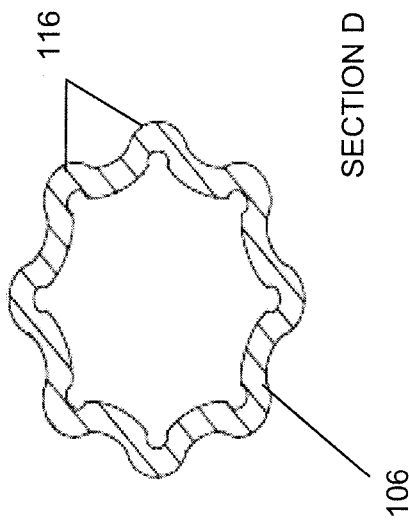
FIG. 3B is a sectional view of the expanding portion of FIG. 3A in accordance with some embodiments of the disclosed subject matter.
Figure 3C:
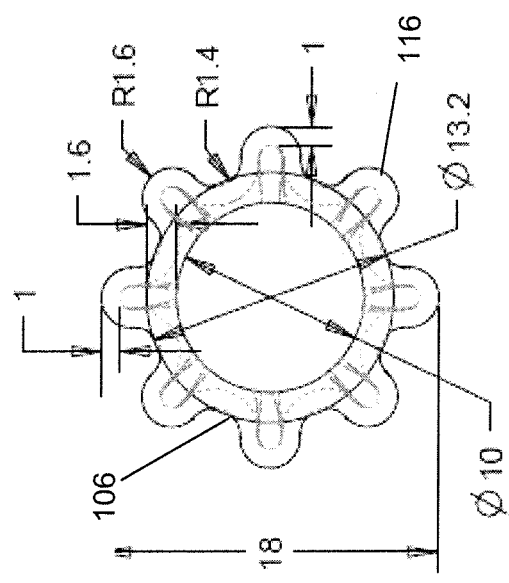
FIG. 3C is a sectional view of the expanding portion of FIG. 3A as expanded into an annulus in accordance with some embodiments of the disclosed subject matter.
Figure 3A:
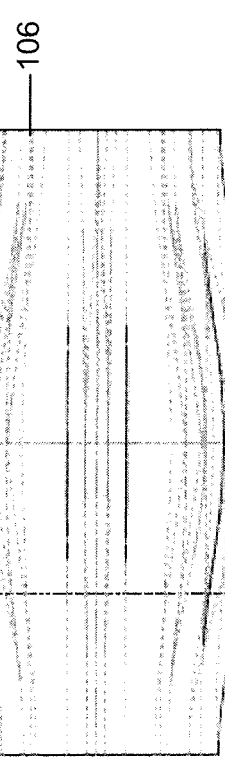
FIG. 3A is a side view of an illustrative expanding portion of an expanding cannula and retractor device in accordance with some embodiments of the disclosed subject matter.

FIG. 3A is a side view of membrane 106 in accordance with some embodiments of the disclosed subject matter. FIG. 3B is a sectional view of the membrane of FIG. 3A as taken through section D. FIG. 3C is another sectional view of membrane 106 in accordance with some embodiments of the disclosed subject matter. Referring to FIGS. 3A-3C, membrane 106 is a continuous structure such that it has no openings that could capture tissue within the expandable portion of cannula 100. As shown by FIGS. 3A-3C, membrane 106 can be a tubular insert having a plurality of ridges 116. In some embodiments, membrane 106 may have the following dimensions: a length of approximately 33 mm, an inner diameter of approximately 10 mm, an outer diameter of approximately 13.2 mm, and a thickness of approximately 1.6 mm. The inner diameter of approximately 10 mm corresponds with the diameter of second tube 104, as shown in FIG. 1D. In some embodiments, membrane 106 may span approximately 20% of the length of device 100. These dimensions for membrane 106 are merely illustrative, and membrane 106 may have any suitable combination of dimensions. For example, the dimensions of membrane 106 may vary depending on the application in which the device 100 is used.

In some embodiments, membrane 106 may be of varying thickness. For example, membrane 106 may be thinnest at the middle of the membrane, and thickest at the ends of the membrane. In some embodiments, membrane 106 may have a thickness of 1 mm at the middle of the membrane, and a thickness of 1.6 mm at the ends of the membrane. The varying thickness of membrane 106 may provide more surface area for expansion of the annulus.

Membrane 106 is generally tubular in shape and has a plurality of ridges 116 along its surface while in the resting position. Ridges 116 allow membrane 106 to expand into annulus 114 without folding over itself. Ridges 116 may be, for example, approximately 1 mm thick and project approximately 2.4 mm from the outer surface of membrane 106. In embodiments in which membrane 106 is of varying thickness, the thickness of ridges 116 may also vary. The dimensions for ridges 116 are merely illustrative, and ridges 116 may have any suitable dimensions. For example, the dimensions for ridges 116 may vary depending on the application in which the device 100 is used.

Membrane 106 is constructed from flexible material such that it can expand into annulus 114, as shown, for example, in FIGS. 1A-1B, and contract into a resting position, as shown, for example, in FIGS. 2A-2C. In some embodiments, membrane 106 can be constructed from, for example, a flexible rubber or silicone material (e.g., a medical-grade silicone material). These materials are merely illustrative, and membrane 106 may be constructed of any suitable material. Because membrane 106 is self-deploying and self-relaxing based on the movements of first and second tubes 102 and 104 relative to each other, cannula 100 does not require an outside form of deflation or inflation. The self-deploying and self-relaxing nature of cannula 100 enhances ease of use and application of cannula 100.

Figure 4:
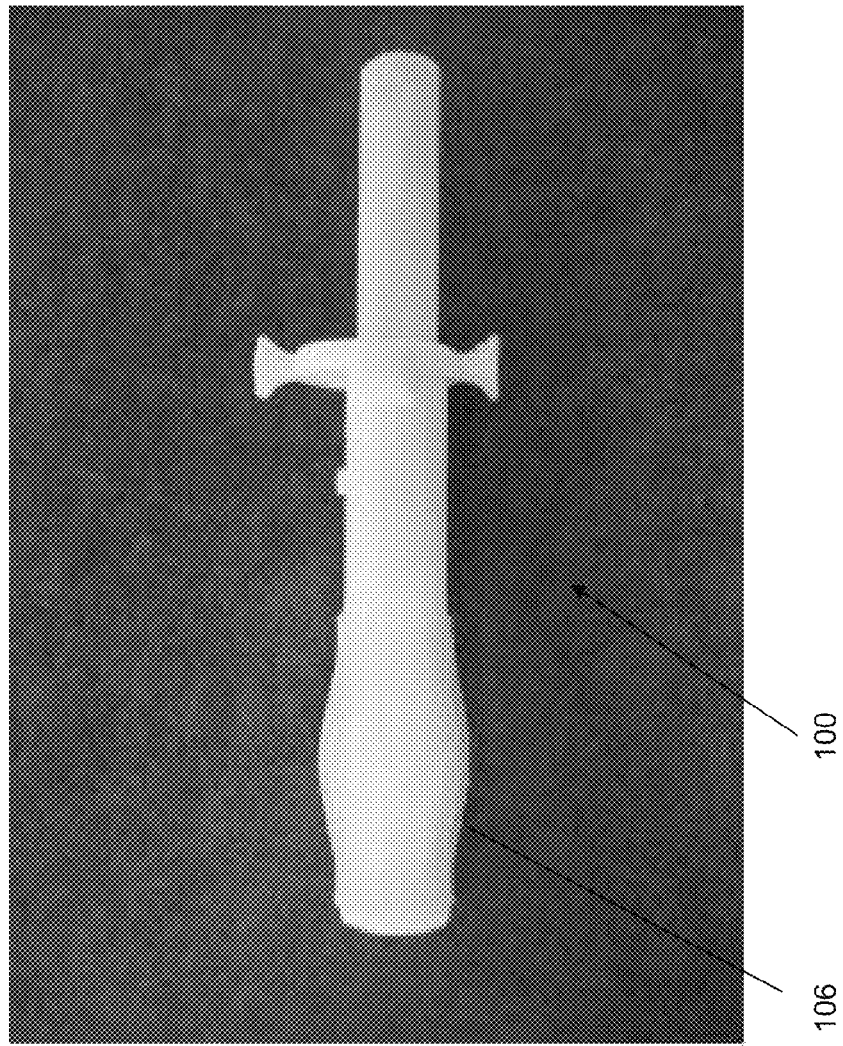
FIG. 4 is a perspective view of an illustrative expanding cannula and retractor device in an unexpanded state in accordance with some embodiments of the disclosed subject matter.
Figure 5:
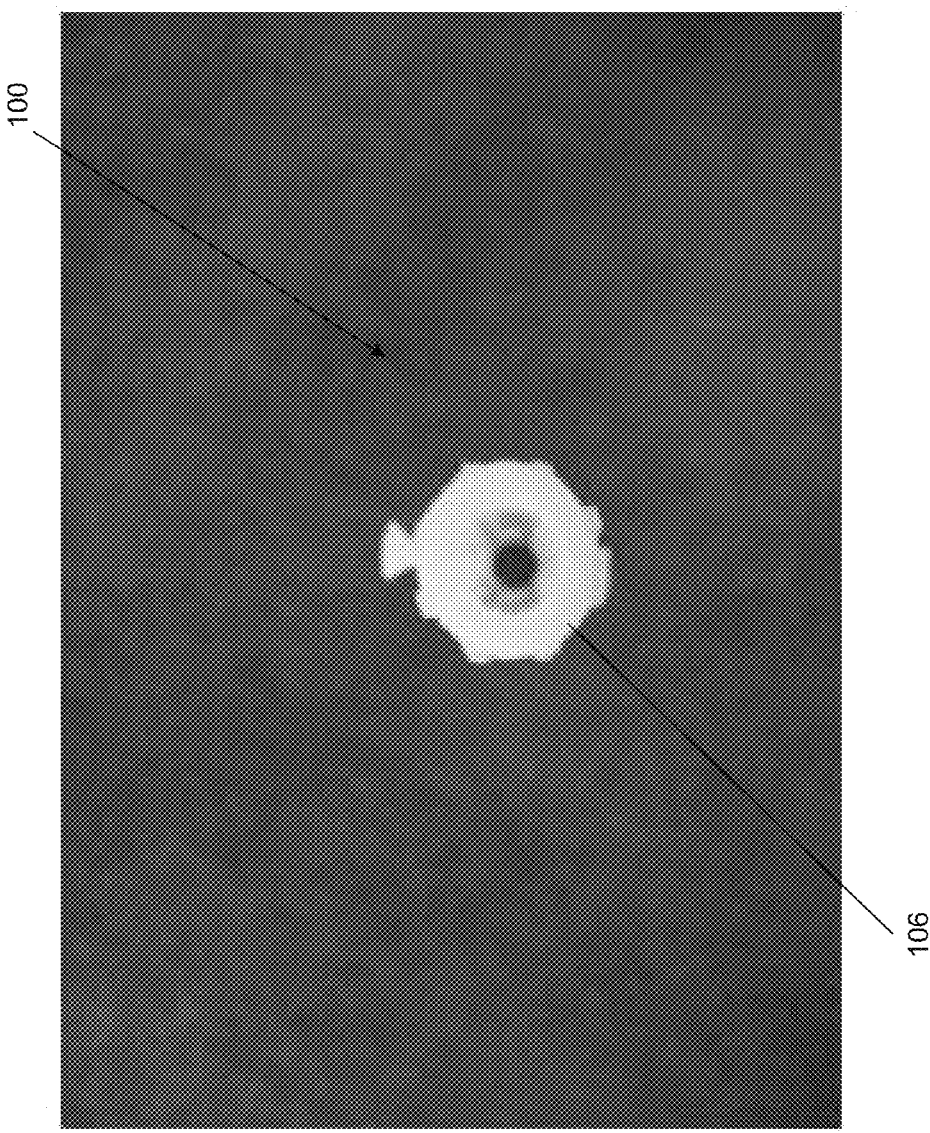
FIG. 5 is an end view of the expanding cannula and retractor device of FIG. 4 in accordance with some embodiments of the disclosed subject matter.

FIG. 4 illustrates cannula 100 with membrane 106 contracted in the resting position in accordance with some embodiments of the disclosed subject matter. FIG. 5 illustrates an end-view of cannula 100 with membrane 106 contracted in the resting position in accordance with some embodiments of the disclosed subject matter. As shown in FIGS. 4 and 5, clip 108 is positioned at the proximal end of second tube 104, such that membrane 106 is in the resting position.

Figure 6:
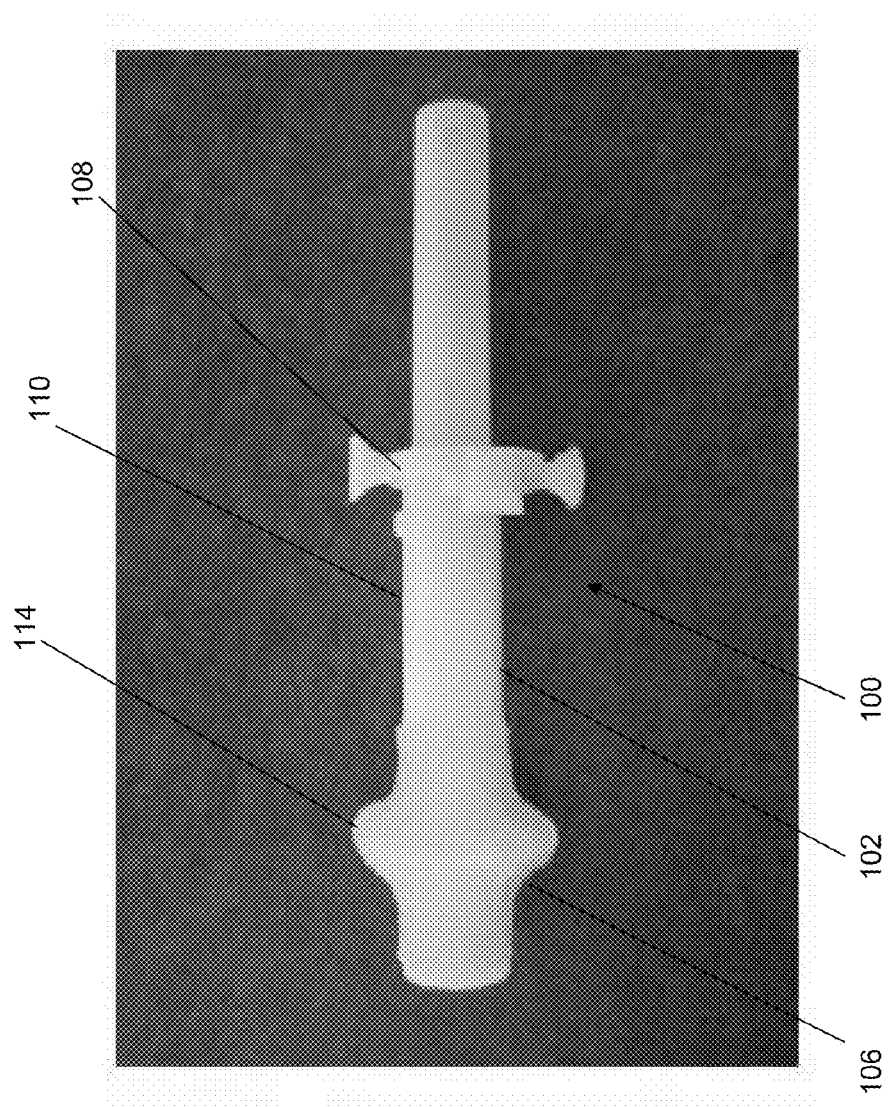
FIG. 6 is a perspective view of the expanding cannula and retractor device of FIG. 4 as expanded into an annulus in accordance with some embodiments of the disclosed subject matter.
Figure 7:
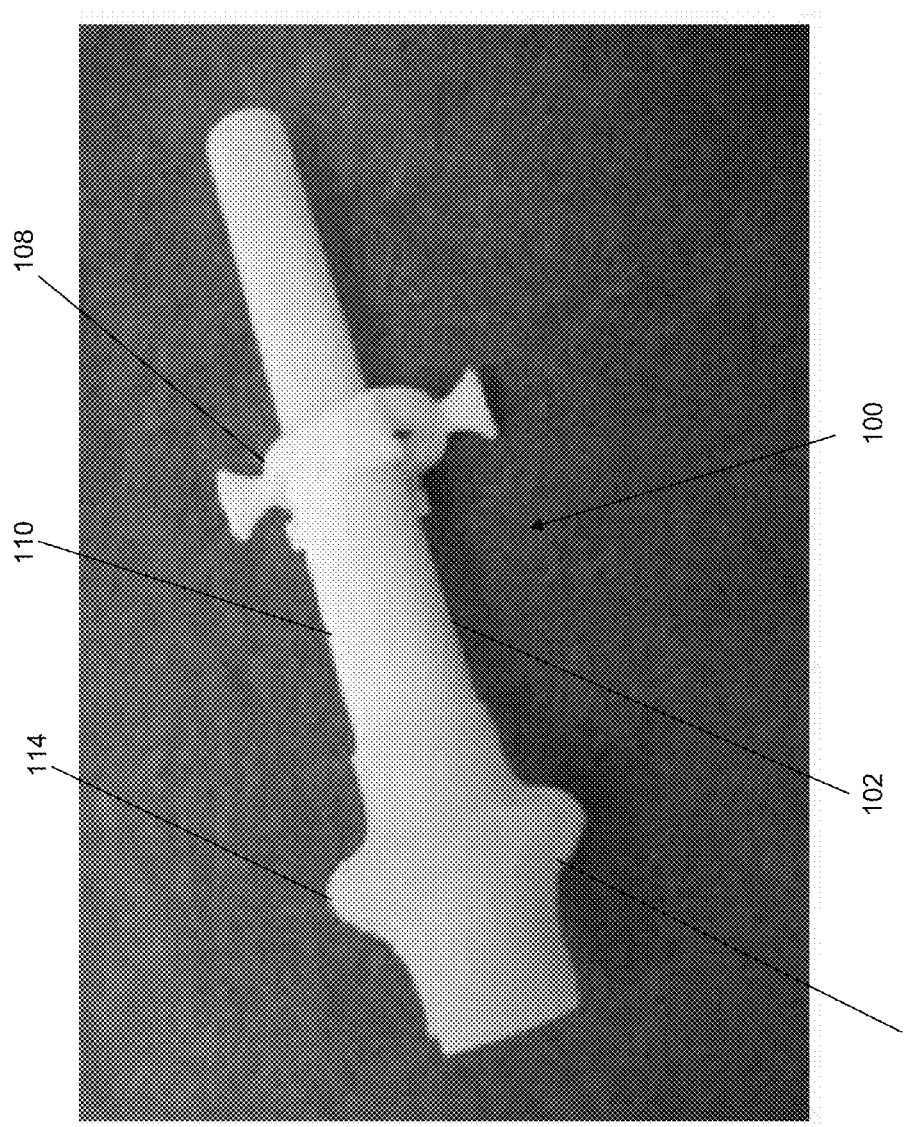
FIG. 7 is another perspective view of the expanding cannula and retractor device of FIG. 4 as expanded into an annulus in accordance with some embodiments of the disclosed subject matter.
Figure 8:
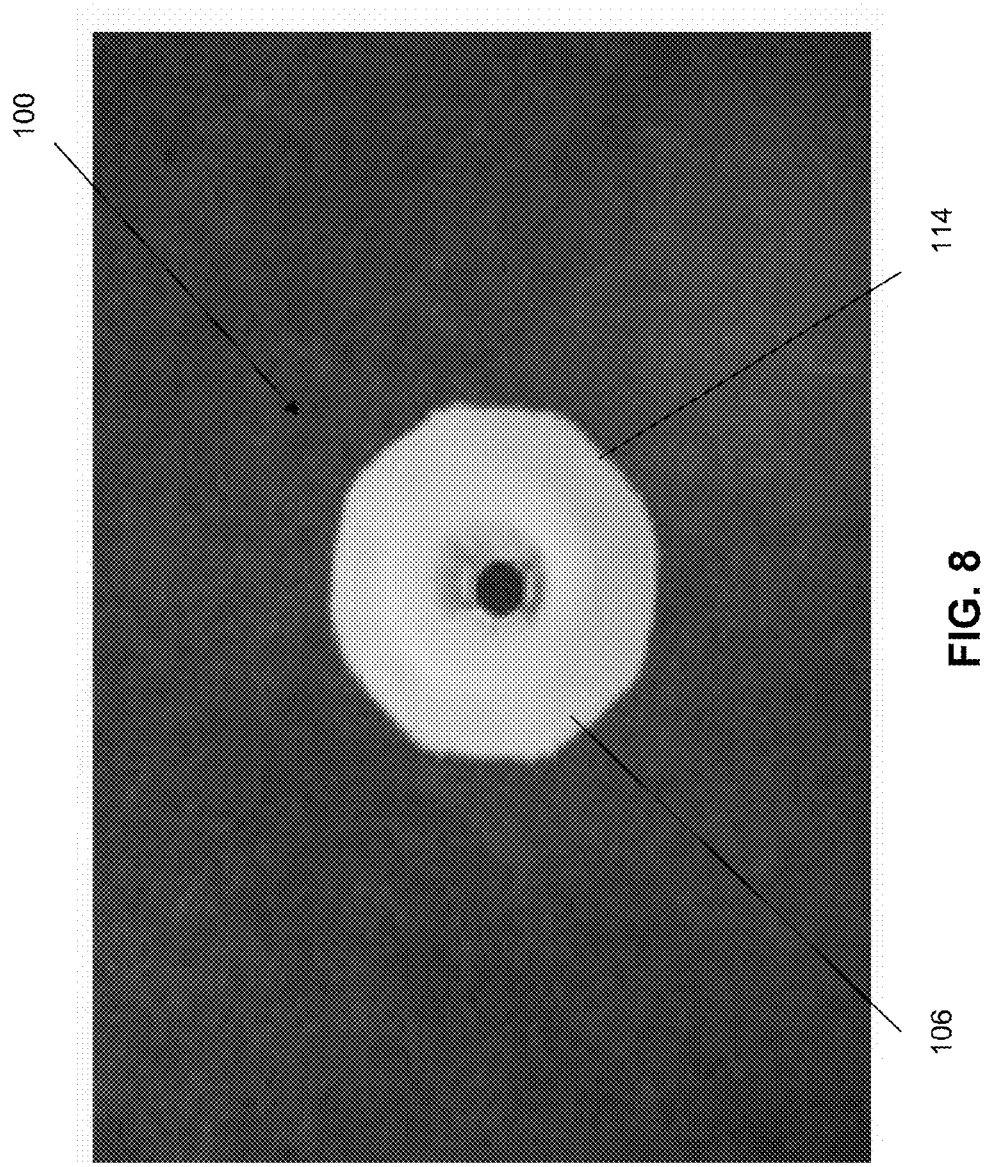
FIG. 8 is an end view of the expanding cannula and retractor device of FIGS. 6-7 in accordance with some embodiments of the disclosed subject matter.

FIGS. 6-7 illustrate cannula 100 with membrane 106 expanded into annulus 114 in accordance with some embodiments of the disclosed subject matter. FIG. 8 illustrates an end-view of cannula 100 with membrane 106 expanded into annulus 114 in accordance with some embodiments of the disclosed subject matter. As shown by FIGS. 6-8, clip 108 has been moved to the distal portion of second tube 104. Moving clip 108 in the distal direction also moves first tube 102 in the distal direction relative to second tube 104. This movement causes membrane 106 to axially compress and radially expand with respect to the axes of first and second tubes 102 and 104, resulting in the formation of annulus 114. In some embodiments, annulus 114 may allow cannula 100 to be used as a retractor to expand working space during a procedure. In some embodiments, annulus 114 may act as a dam against the extravasation of fluid or gas used to inflate, and provide a viewing milieu, in the working space.

Figure 9:
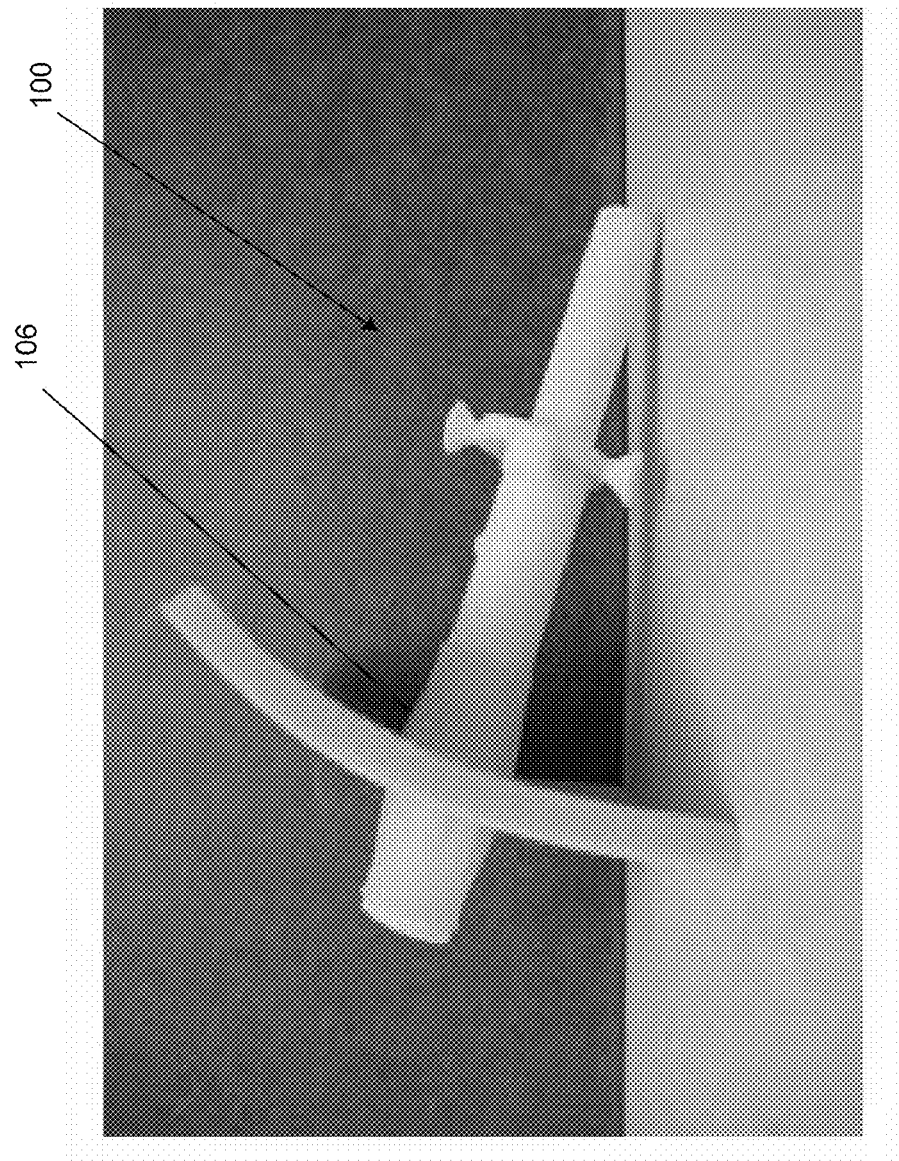
FIG. 9 is a perspective view of an expanding cannula and retractor device in an unexpanded state and as received within tissue in accordance with some embodiments of the disclosed subject matter.
Figure 10:
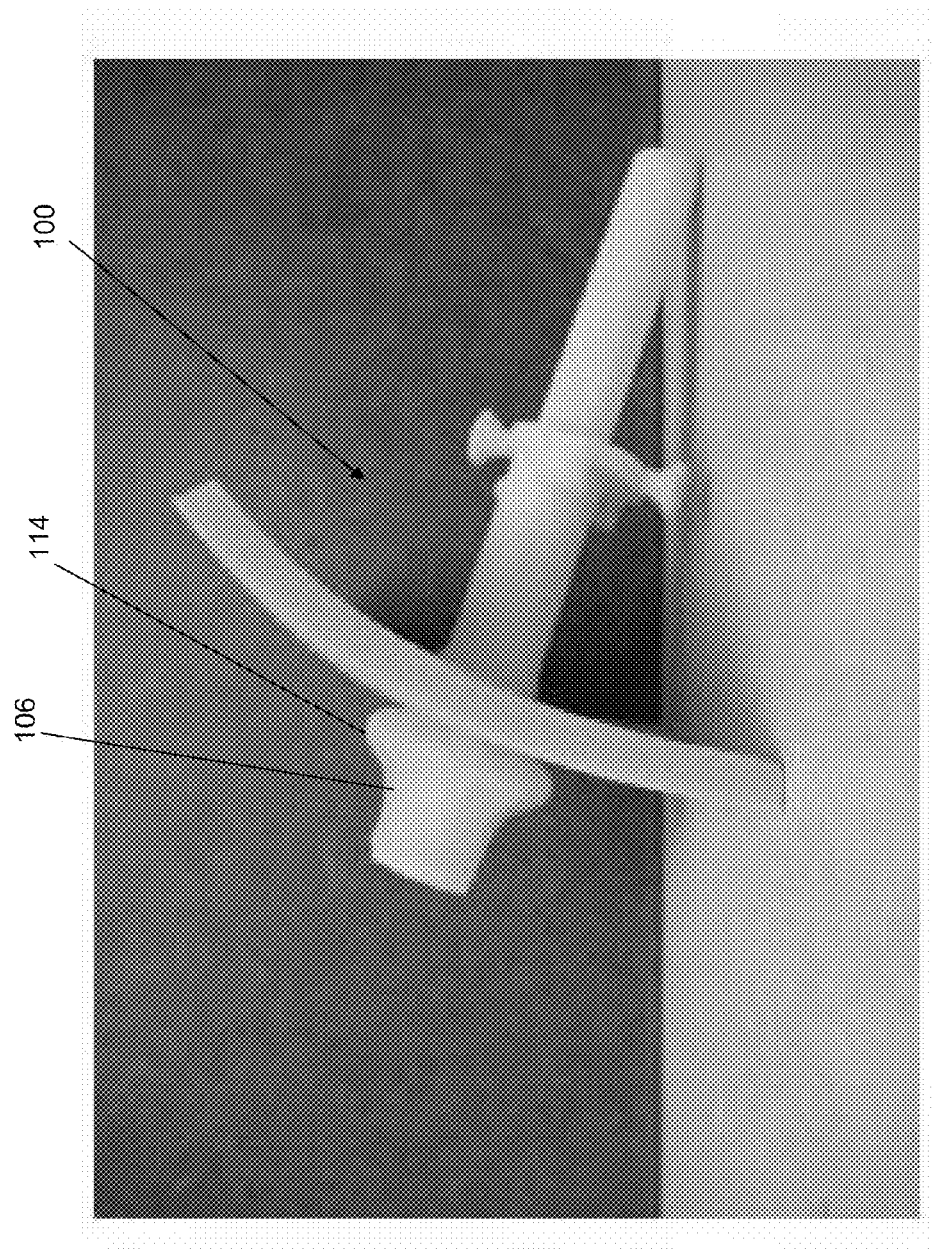
FIG. 10 is a perspective view of the expanding cannula and retractor device of FIG. 9 as expanded into an annulus in accordance with some embodiments of the disclosed subject matter.
Figure 12A:
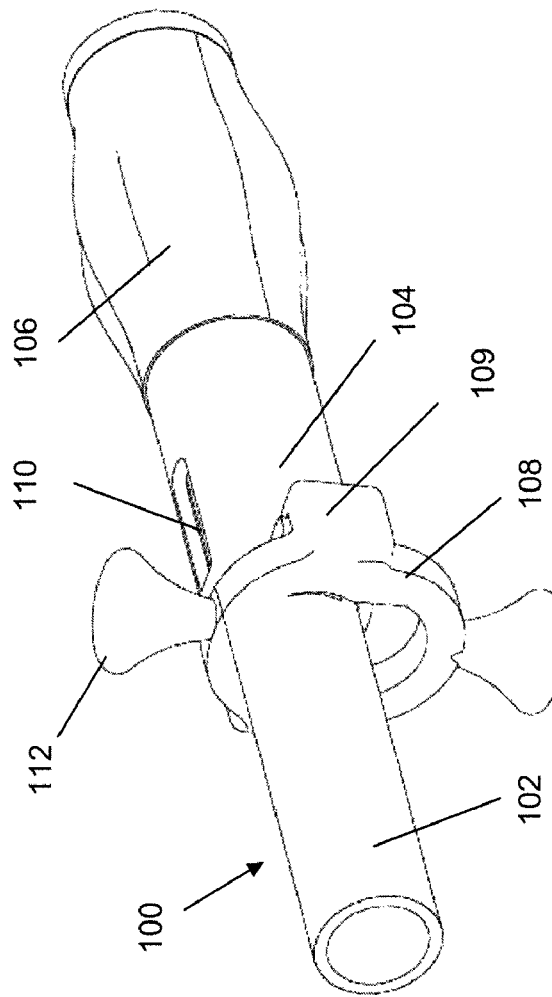
FIGS. 12A-12D are perspective, side, and sectional views illustrating an unlocked position for a clip of an expanding cannula and retractor device in accordance with some embodiments of the disclosed subject matter.
Figure 12B:
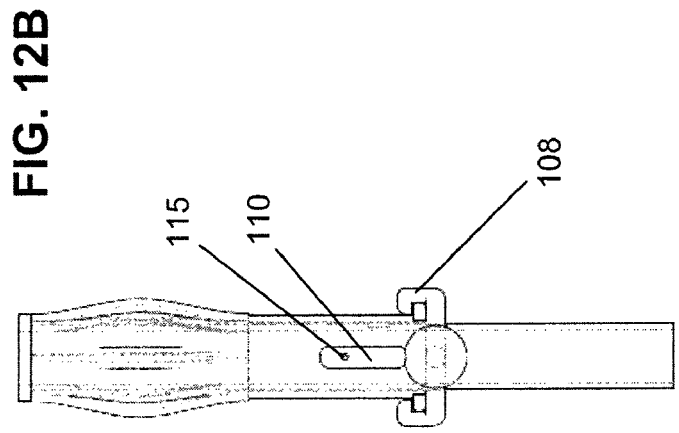
Figure 12C:
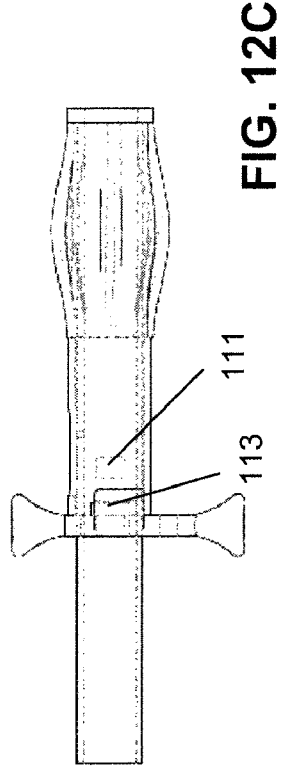
Figure 12D:
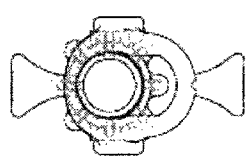

FIG. 9 illustrates cannula 100 as received within the skin and tissue with membrane 106 contracted in the resting position in accordance with some embodiments of the disclosed subject matter. FIG. 10 illustrates cannula 100 as received within the skin and tissue with membrane 106 expanded into annulus 114 in accordance with some embodiments of the disclosed subject matter. As shown in FIGS. 9 and 10, expansion of membrane 106 into annulus 114 may act as a restraint against unintentional extraction of cannula 100 during an arthroscopic and/or laparoscopic procedure.

Once a procedure is completed, membrane 106 is contracted into its resting position, as shown, for example, in FIG. 9, so that cannula 100 may be extracted. In order to contract membrane 106, clip 108 is moved toward the proximal end of second tube 104 so that first tube 102 is moved relative to second tube 104. Moving first tube 102 in this manner pulls membrane 106 with it, causing membrane 106 to contract back to its resting position.

It will be understood that the foregoing is only illustrative of the principles of the invention, and that various modifications can be made by those skilled in the art without departing from the scope and spirit of the invention.

What is claimed is:

1. An expanding cannula and retractor device for insertion through tissue, comprising:
   a first tube;
   a second tube disposed within the first tube; and
   a continuous membrane disposed between and connecting a distal portion of the first tube to a distal portion of the second tube, wherein the membrane expands into an annulus by the relative movement of the second tube with respect to the first tube, the annulus configured to contact the tissue to maintain the position of the device with respect to the tissue, wherein the continuous membrane comprises a tubular insert formed as a single unitary structure and disposed between the first and second tubes, the insert having a plurality of preformed ridges extending along a length of the insert, the ridges being present in a contracted, rest position of the continuous membrane.

2. The device of claim 1, wherein the first tube remains stationary and the movement of the second tube causes the membrane to expand into the annulus.

3. The device of claim 1, wherein the second tube remains stationary and the movement of the first tube causes the membrane to expand into the annulus.

4. The device of claim 1, wherein, following the formation of the annulus, the membrane contracts by relative movement of the second tube with respect to the first tube.

5. The device of claim 4, wherein the first tube remains stationary and the movement of the second tube causes the membrane to contract.

6. The device of claim 4, wherein the second tube remains stationary and the movement of the first tube causes the membrane to contract.

7. The device of claim 1, wherein the second tube is disposed concentrically within the first tube.

8. The device of claim 1, wherein the device has a length, and wherein the tubular insert spans about 20% of the length of the device.

9. The device of claim 1, wherein the annulus is formed by the compression of the tubular insert.

10. The device of claim 9, wherein the ridges prevent the membrane from folding over itself during formation of the annulus.

11. The device of claim 1, further comprising a clip that is slidably mounted on the first tube and coupled to the second tube, wherein movement of the clip controls the relative movement of the second tube with respect to the first tube.

12. The device of claim 11, wherein the first tube further comprises a recess that spans a distance on an outer surface of the first tube, the distance corresponding to the distance travelled by the second tube to fully expand the membrane into the annulus.

13. The device of claim 11, wherein movement of the clip along the first tube in the direction of the distal portion of the first tube causes the membrane to expand into the annulus from a resting position.

14. The device of claim 11, wherein movement of the clip away from the distal portion of the first tube causes the membrane to contract into a resting position.

15. The device of claim 11, further comprising a locking mechanism coupled to the clip, wherein the locking mechanism prevents the clip from sliding along the first tube when engaged.

16. The device of claim 11, further comprising a locking mechanism coupled to the clip, wherein the locking mechanism prevents the membrane from expanding or contracting when engaged.

17. The device of claim 1, wherein the first and second tubes are constructed from at least one of a rigid plastic material and a metallic material.

18. The device of claim 1, wherein an outer diameter of each of the first and second tubes ranges from 5-10 mm.

19. The device of claim 1, wherein the membrane is constructed from at least one of a flexible rubber material and a silicone material.

20. An expanding cannula and retractor device for insertion through tissue, comprising:
   a first tube;
   a second tube disposed within the first tube, wherein the second tube includes a first locking slot formed in an outer surface thereof and a second locking slot formed in the outer surface thereof and spaced longitudinally from the first locking slot;
   a continuous membrane disposed between and connecting a distal portion of the first tube to a distal portion of the second tube, wherein the membrane expands into an annulus by the relative movement of the second tube with respect to the first tube, the annulus configured to contact the tissue to maintain the position of the device with respect to the tissue; and
   a clip that is slidably mounted on the first tube for locking the second tube in place relative to the first tube so as to prevent axial movement of the second tube relative to the first tube, the clip having an opening that receives the second tube so as to permit the clip to move in a lateral direction that is perpendicular to a longitudinal axis of the first tube for locking and unlocking the second tube relative to the first tube, the opening of the clip being defined by a first section in which the second tube is received and can slide axially therethrough and a second section in which the second tube is received only when one of the first and second locking slots is in registration therewith, wherein when the second tube is received within the second section, axial movement of the second tube relative to the first tube is prevented and the second tube is locked in place.

21. The device of claim 20, wherein the first section of the opening has a circular shape complementary to a circular shape of the second tube and the second section of the opening is defined by a pair of opposing parallel walls that mate with flats formed in one of the first and second locking slots.

22. The device of claim 21, a distance between the opposing parallel walls is less than an outer diameter of a circular portion of the second tube that is outside of the first and second locking slots so as to prevent the circular portion of the second tube from being received therein.

23. The device of claim 20, wherein the first locking slot is located closer to a proximal end of the second tube compared to the first tube and the second locking slot is located closer to a distal end of the second tube, the first locking slot for locking the second tube in a first position in which the continuous membrane is in a contracted state and the second locking slot for locking the second tube in a second position in which the continuous membrane is in an expanded state and the annulus is formed.

24. The device of claim 20, wherein the continuous membrane comprises a tubular insert formed as a single unitary structure and disposed between the first and second tubes, the insert having a plurality of preformed ridges extending along a length of the insert, the ridges being present in a contracted, rest position of the continuous membrane.

* * * * *